United States Patent

Chen et al.

[11] Patent Number: 4,965,200
[45] Date of Patent: Oct. 23, 1990

[54] PROCESS FOR THE PREPARATION OF 3-KETO, 5-HYDROXY SIMVASTATIN ANALOGS

[75] Inventors: Shieh-Shung J. Chen, Morganville; Byron H. Arison, Watchung, both of N.J.

[73] Assignee: Merck & Co., Inc., Rahway, N.J.

[21] Appl. No.: 370,488

[22] Filed: Jun. 23, 1989

[51] Int. Cl.$^5$ .................. C12P 17/06; C12R 1/645
[52] U.S. Cl. .................. 435/125; 435/253.5; 435/886
[58] Field of Search .................. 435/125, 886, 253.5

[56] References Cited

U.S. PATENT DOCUMENTS

| | | | |
|---|---|---|---|
| 4,448,979 | 5/1984 | Terahara et al. | 549/292 |
| 4,517,373 | 5/1985 | Terahara et al. | 549/292 |
| 4,537,859 | 8/1985 | Terahara et al. | 435/146 |
| 4,921,974 | 5/1990 | Duggan | 549/214 |

FOREIGN PATENT DOCUMENTS 59-186972 10/1984 Japan .
2075013 4/1981 United Kingdom .

OTHER PUBLICATIONS

U.S. Pat. application Ser. No. 213,010, filed 6/29/88.
U.S. Pat. application Ser. No. 250,646, filed 9/29/88.

*Primary Examiner*—Herbert J. Lilling
*Attorney, Agent, or Firm*—Melvin Winokur; Joseph F. DiPrima

[57] ABSTRACT

A biotransformation for the formation of a 3-keto-5-hydroxy simvastation analog (I) or a 8-acyloxy derivative thereof is disclosed.

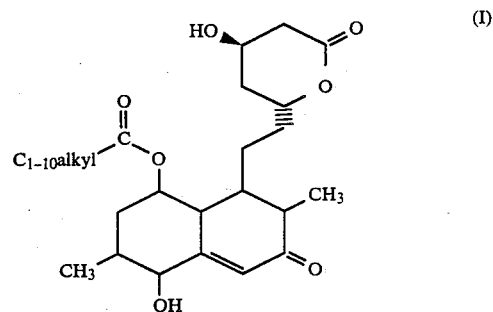

4 Claims, No Drawings

PROCESS FOR THE PREPARATION OF 3-KETO, 5-HYDROXY SIMVASTATIN ANALOGS

BACKGROUND OF THE INVENTION

Hypercholesterolemia is known to be one of the prime risk factors for atherosclerosis and coronary heart disease, the leading cause of death and disability in western countries. The bile acid sequestrants seem to be moderately effective as antihypercholesterolemic agents but they must be consumed in large quantities, i.e., several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof. For example, simvastatin wherein the 8-acyl moiety is 2,2-dimethylbutyryl is an even more potent HMG-CoA reductase inhibitor than lovastatin.

The naturally occurring compounds and their semi-synthetic analogs have the following general structural formulae:

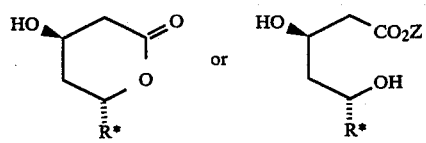

wherein:

Z is hydrogen, $C_{1-5}$ alkyl or $C_{1-5}$ alkyl substituted with a member of the group consisting of phenyl, dimethylamino, or acetylamino; and R* is:

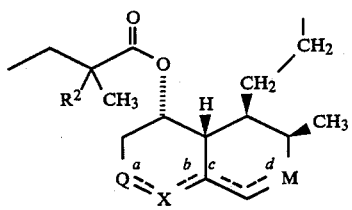

wherein
Q is

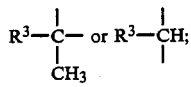

$R^3$ is H or OH;
M is

$R^4$ is hydrogen or hydroxy;
X is $CR^5R^6$, O, S, or NH; $R^5$ and $R^6$ are H, OH, or $OR^7$ where $R^7$ represents a phosphoryl or acyl moiety;

$R^2$ is hydrogen or methyl; and a, b, c, and d represent single bonds, one of a, b, c or d represents a double bond, or both a and c or both b and d represent double bonds provided that when a is a double bond, Q is

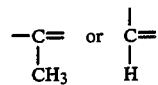

and when d is a double bond, M is

and provided that when $R^5$ or $R^6$ is OH or $OR^7$ or X is O, S, or NH, a, b, and c are single bonds.

U.S. Pat. No. 4,517,373 discloses semi-synthetic hydroxy containing compounds represented by the above general formula wherein R* is

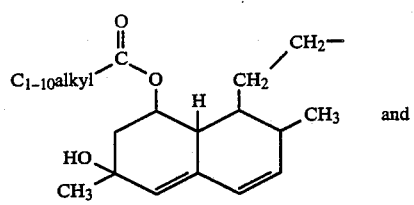

and

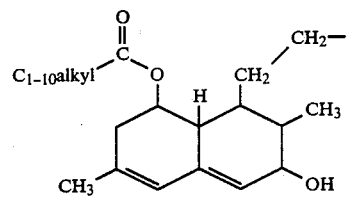

U.S. Pat. No. 4,537,859 and U.S. Pat. No. 4,448,979 also disclose semi-synthetic hydroxy-containing compounds represented by the above general formula wherein R* is

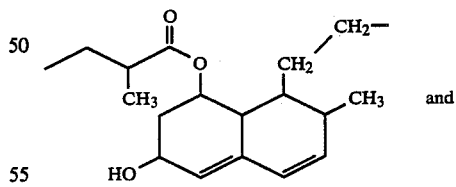

and

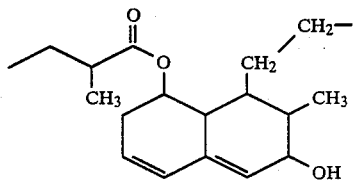

These compounds are prepared by the action of certain microorganisms on the corresponding non-hydroxylated substrates. One such organism described in U.S. Pat. No. 4,537,859 is of the genus Nocardia.

Copending U.S. patent application Ser. No. 213,010 filed Jun. 29, 1988 discloses 5-oxygenated compounds of the above formula wherein R* is:

wherein $R_5$ and $R_6$ independently are H, OH or an oxygenated derivative $OR_7$ provided that one and only one of $R_5$ and $R_6$ is OH or $OR_7$.

Copending U.S. patent application Ser. No. 250,646 filed Sept. 29, 1988 discloses a chemical methodology to the 5-oxygenated compounds described above.

British patent GB No. 2,075,013 discloses compounds of the above formula wherein R* is:

wherein A amongst other groups is C=O, B amongst other groups is —CHOR³ in which R³ represents an H or a acyl group, R¹ is an H or a methyl group and R² is an H or a acyl group. The 3-keto, 5-hydroxy compound in this disclosure is formed in minor amounts from a chemical oxidation of the hexahydro starting material.

DETAILED DESCRIPTION OF THE INVENTION

The instant invention is a novel process for the preparation of 3-keto, 5-hydroxy derivatives of simvastatin and analogs thereof (I) using a microorganism MA6578 tentatively indentified as a Streptomyces sp.

The process involves the bioconversion of substrate (II) with the microorganism MA6578.

The acyl moiety $$C_{1-10}alkyl\text{-}C\text{—}$$

can be branched or straight, preferably it is 2-methylbutyryl or 2,2-dimethylbutyryl, most preferably 2,2-dimethylbutyryl.

The characteristics of microorganism MA6578 tentatively identified as Streptomyces sp. are described below:

Microscopic observations—Culture grows as branched filaments 0.4–0.6 microns diameter. Spherical to oval spores borne in lossely coiled or looped chains.

Oat Meal Agar

Vegatative Growth: Hyaline
Aerial Mass: Good growth, powdery, off-white to medium slate gray
Soluble Pigment: None

Glycerol-Asparagine

Vegetative Growth: Hyaline
Aerial Mycelium: Very sparse, powdery, white to slate gray
Soluble Pigment: None

Inorganic Salts-Starch Agar

Vegetative Growth: Hyaline
Aerial Mass: Good growth, powdery, white to medium slate gray
Aerial Mycelium: None
Soluble Pigment: Clearing of starch at periphery of colonies

Yeast Extract-Malt Extract Agar

Vegetative Growth: Reverse: yellow-brown
Aerial Mass: Abundant, powdery to velvety, light gray to slate gray
Soluble Pigment: Yellow-brown

Egg Albumin Agar

Vegetative Growth: Hyaline to off white
Aerial Mass: Sparse, powdery, off white to medium gray
Soluble Pigment: None

Nutrient Tyrosine Agar

Vegetative Growth: Hyaline
Aerial Mass: Abundant, white-gray, powdery
Soluble Pigment: None
Decomposition of tyrosine: Positive

Skim Milk Agar

Vegetative Growth: Hyaline, flat, matte growth
Aerial Mass: None
Soluble Pigment: None
Hydrolysis of casein: Positive

Tomato Paste Oatmeal Agar

Aerial Mass: good, powdery, light to dark gray

Gelatin Stabs

Vegetative Growth: Off white, fluffy Aerial Mass: Present
Soluble Pigment: None
Liquification of gelatin: Positive

Peptone-Iron-Yeast Extract Agar Slants

Vegetative Growth: Hyaline
Aerial Mass: None
Soluble Pigment: None
Melanin: Negative
$H_2S$: Negative

Tryptone Yeast Extract Broth

Soluble Pigment: None

| Carbohydrate utilization pattern | | | | | |
| --- | --- | --- | --- | --- | --- |
| d-glucose | ++ | d-maltose | ++ | sucrose | − |
| d-arabinose | − | d-mannitol | − | d-xylose | − |
| l-arabinose | − | d-mannose | ++ | l-xylose | − |
| d-fructose | − | d-mannose | − | alpha d-lactose | + |
| l-glucose | +/− | d-raffinose | − | beta d-lactose | + |
| inositol | − | l-rhamnose | − | | |

Carbon source utilization studies were carried out using Pridham and Gottlieb basal medium supplemented with 1% carbon source. Scoring was graded according to the methods described in "Methods for Characterization of Streptomyces species", IJSB 16: pps 313–340

Tentative identification—Streptomyces sp.

The compounds (I) are prepared in the instant process from the sodium salt of simvastatin, lovastatin or an analog having a 6-methyl group by one of the following methods:

(a) adding the substrate to a growing culture of streptomyces sp. for a suitable incubation period followed by isolation, and derivatization if desired;

(b) collecting a culture of the bioconverting microorganism and contacting the collected cells with the substrate.

Cultivation of the bioconverting microorganism MA6578 tentatively identified as a Streptomyces sp. can be carried out by conventional means in a conventional culture medium containing nutrients well known for use with such microorganisms. Thus, as is well known, such culture media contain sources of assimilable carbon and of assimilable nitrogen and often inorganic salts. Examples of sources of assimilable carbon include glucose, sucrose, starch, glycerin, millet jelly, molasses and soybean oil. Examples of sources of assimilable nitrogen include soybean solids (including soybean meal and soybean flour), wheat germ, meat extracts, peptone, corn steep liquor, dried yeast and ammonium salts, such as ammonium sulphate. If required, inorganic salts, such as sodium chloride, potassium chloride, calcium carbonate or phosphates, may also be included. Also, if desired, other additives capable of promoting the production of hydroxylation enzymes may be employed in appropriate combinations. The particular cultivation technique is not critical to the process of the invention and any techniques conventionally used for the cultivation of microorganisms may be employed with the present invention. In general, of course, the techniques employed will be chosen having regard to industrial efficiency. Thus, liquid culture is generally preferred and the deep culture method is most convenient from the industrial point of view.

Cultivation will normally be carried out under aerobic conditions and at a temperature within the range from 20° to 37° C., more preferably from 26° to 28° C.

Method (a) is carried out by adding the substrate to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the microorganism begins to increase and this is usually 1 or 2 days after beginning cultivation of the microorganism. The amount of the substrate added is preferably from 0.01 to 5.0% by weight of the medium, more preferably from 0.05 to 0.5%, e.g., from 0.05 to 0.1% by weight. After addition of the substrate, cultivation is continued aerobically, normally at a temperature within the ranges proposed above. Cultivation is normally continued for a period of from 1 to 2 days after addition of the substrate.

In method (b), cultivation of the microorganism is first carried out under conditions such as to achieve its maximum hydroxylation capacity; this capacity usually reaches a maximum between 4 and 5 days after beginning the cultivation, although this period is variable, depending upon the nature and temperature of the medium, the species of microorganism and other factors. The hydroxylation capacity of the culture can be monitored by taking samples of the culture at suitable intervals, determining the hydroxylation capacity of the samples by contacting them with a substrate under standard conditions and determining the quantity of product obtained and plotting this capacity against time as a graph. When the hydroxylation capacity has reached its maximum point, cultivation is stopped and the microbial cells are collected. This may be achieved by subjecting the culture to centrifugal separation, filtration or similar known separation methods. The whole cells of the cultivating microorganism thus collected, preferably, are then washed with a suitable washing liquid, such as physiological saline or an appropriate buffer solution.

Contact of the collected cells of the microorganism MA6578 with the substrate is generally effected in an aqueous medium, for example in a phosphate buffer solution at a pH value of from 5 to 9. The reaction temperature is preferably within the range from 20° to 45° C., more preferably from 25° to 30° C. The concentration of the substrate in the reaction medium is preferably within the range from 0.01 to 5.0% by weight. The time allowed for the reaction is preferably from 1 to 5 days, although this may vary depending upon the concentration of the substrate in the reaction mixture, the reaction temperature, the hydroxylation capacity of the microorganism (which may, of course, vary from species to species and will also, as explained above, depend upon the cultivation time) and other factors.

The microorganism useful in the novel process of this invention has been tentatively as Streptomyces sp. A sample of the culture designated ATCC 53898 has been deposited (Apr. 18, 1989) in the permanent culture collection of the American Type Culture Collection at 12301 Parklawn Drive, Rockville, MD 20852.

After completion of the conversion reaction by any of the above methods, the desired compound can be directly isolated, separated or purified by conventional means. For example, separation and purification can be effected by filtering the reaction mixture, extracting the resulting filtrate with a water-immiscible organic solvent (such as ethyl acetate), distilling the solvent from the extract, subjecting the resulting crude compound to column chromatography, (for example on silica gel or alumina) and eluting the column with an appropriate eluent, especially in an HPLC apparatus.

The following examples illustrate the preparation of these compounds and, as such, are not to be construed as limiting the invention set forth in the claims appended hereto.

The composition of media employed in the following examples are listed below.

|  | (g/L) |
| --- | --- |
| Seed Medium A |  |
| Glucose | 1.0 |
| Dextrin | 10.0 |
| Beef extract | 3.0 |
| Ardamine PH | 5.0 |
| NZ Amine Type E | 5.0 |
| MgSO4.7H2O | 0.05 |
| K2HPO4 | 0.37 |
| Adjust pH to 7.1 |  |
| Add CaCO3 | 0.5 g/l |
| Transformation Medium B |  |
| Mannitol | 5 |
| Glycerol | 5 |
| Hycase SF | 2 |
| Beef extract | 1 |
| Corn steep liquor | 3 |
| Adjust pH to 7.0 |  |

EXAMPLE 1

Preparation of 6(R)-[2-[8(S)-(2,2-dimethylbutyryloxy)-2(S), 6(R)-dimethyl-3-oxo-5-hydroxy-1,2,5,6,7,8,8a(R)-heptahydronaphthyl-1(S)]ethyl]-4(R)-hydroxy-3,4,5,6-tetrahydro-2H-pyran-2-one

A. Culture Conditions and Bioconversion

Seed cultures (MA6578) were prepared in medium A (50 ml in a 250 ml 3-baffle Erlenmeyer flask). The seed flasks were incubated on a rotary shaker (220 rpm) at 27° C. for 24 hours. Transformation flasks (50 ml medium B in 250 ml Erlenmeyer flask) were inoculated with 2.5 ml of seed culture and incubated at 27° C. on a rotary shaker. After 24 hours the transformation flask was charged with 10 mg of sodium 7-[1,2,6,7,8,8a(R)-hexahydro-2(S)-methyl-6(R)-methyl-8(S)-(2,2-dimethylbutyryloxy)-1(S)-naphthyl]-3(R),5(R)-dihydroxyheptanoate (sodium salt). The cultures were then incubated for 48 hours. Following incubation, the whole broth was extracted as described below.

B. Isolation

The filtered broth, prepared as above, at pH 8.5 was extracted with two 50 ml portions of ethyl acetate. The aqueous layer was adjusted to pH 3 with 1N HCl and extracted with four 50 ml portions of ethyl acetate. The ethyl acetate layers were combined and dried over sodium sulfate and evaporated to a brown oil. The oil was dissolved in 50 ml CH2Cl2 and two drops of CF3COOH were added. After one hour at 50° C. the reaction mixture was evaporated and redissolved in a small portion of acetonitrile and further purified by HPLC on a Whatman Partisil, 10 ODS-3 column. The column was developed with 45% aqueous acetonitrile. The fractions at a retention time of 7.95 minutes were pooled and the solvent was evaporated to yield the titled compound which was characterized by its NMR spectrum.

$^1$H NMR(CDCl$_3$) δ6.07(d, J=2 Hz, 1H), 5.41(q, J≈2, 1H), 4.49(m, 1H), 4.35(qn, J≈4, 1H), 4.14(d, J=4.5, 1H), 2.90(m, 1H), 2.80(dq, J=7, 5, 1H), 2.69(dd, J=18.0, 4.5, 1H) 2.62(ddd, J=18.0, 3.5, 1.5, 1H) 2.10(m, 1H), 1.52(m, 2H), 1.10(s, 6H), 1.05(d, J=7, 3H), 1.04(d, J=7, 3H), 0.81(t, J=7.5, 3H).

What is claimed is:

1. A process for the preparation of a compound represented by the formulae (I)

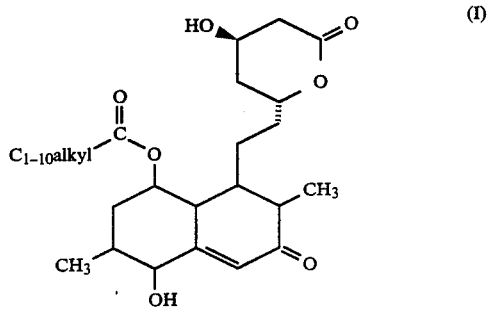

which comprises culturing a microorganism Streptomyces sp. (MA6578) (ATCC 53898) in a nutrient medium containing assimilable sources of nitrogen and carbon and the sodium salt (II):

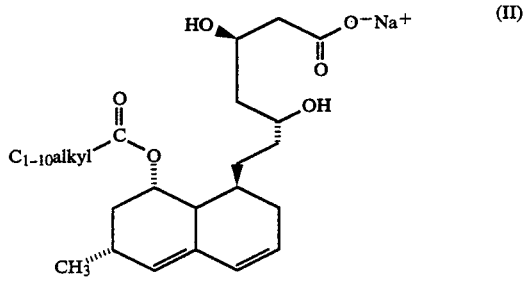

under aerobic conditions until a substantial amount of the compound is produced and isolating the compound so produced.

2. A process of claim 1 in which

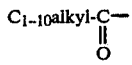

is 2-methylbutyryl or 2,2-dimethylbutyryl.
  3. A process of claim 2 in which
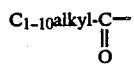
is 2,2-dimethylbutyryl.
  4. A process of claim 2 in which
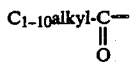
is 2-methylbutyryl.